(12) United States Patent
Egan

(10) Patent No.: US 7,316,716 B2
(45) Date of Patent: Jan. 8, 2008

(54) GASTRIC BYPASS PROSTHESIS

(75) Inventor: Thomas D. Egan, Marblehead, MA (US)

(73) Assignee: Gastrix Medical, LLC, Marblehead, MA (US)

( * ) Notice: Subject to any disclaimer, the term of this patent is extended or adjusted under 35 U.S.C. 154(b) by 0 days.

(21) Appl. No.: 10/511,385

(22) PCT Filed: May 9, 2003

(86) PCT No.: PCT/US03/14885

§ 371 (c)(1),
(2), (4) Date: Oct. 15, 2004

(87) PCT Pub. No.: WO03/094785

PCT Pub. Date: Nov. 20, 2003

(65) Prior Publication Data

US 2005/0256587 A1    Nov. 17, 2005

(51) Int. Cl.
*A61F 2/04* (2006.01)

(52) U.S. Cl. ................................................. 623/23.65

(58) Field of Classification Search .. 623/23.65–23.68; 600/37; 606/213–217, 139, 192
See application file for complete search history.

(56) References Cited

U.S. PATENT DOCUMENTS

| | | | | |
|---|---|---|---|---|
| 4,134,405 A | * | 1/1979 | Smit | 606/108 |
| 5,246,456 A | | 9/1993 | Wilkinson | 623/12 |
| 5,306,300 A | | 4/1994 | Berry | 623/11 |
| 5,820,584 A | * | 10/1998 | Crabb | 604/500 |
| 6,302,917 B1 | * | 10/2001 | Dua et al. | 623/23.68 |
| 6,409,656 B1 | * | 6/2002 | Sangouard et al. | 600/30 |
| 6,432,040 B1 | | 8/2002 | Meah | 600/37 |
| 6,540,789 B1 | | 4/2003 | Silverman et al. | 623/23.65 |
| 6,675,809 B2 | * | 1/2004 | Stack et al. | 128/898 |

(Continued)

FOREIGN PATENT DOCUMENTS

| WO | 03/086246 | 10/2003 |
|---|---|---|
| WO | 03/086247 | 10/2003 |

OTHER PUBLICATIONS

International Search Report dated Aug. 15, 2003.

*Primary Examiner*—Suzette Gherbi
(74) *Attorney, Agent, or Firm*—Mark G. Lappin; Foley & Lardner LLP

(57) ABSTRACT

A device (10) for treatment of obesity of a patient comprises an annular element (12) having a relatively large outer boundary and a relatively small inner boundary, and an elongated flexible tube (14) extending from the relatively small inner boundary of the annular element to a distal end. The relatively large outer boundary is adapted to be attached to an inner wall of a stomach (100) of a patient, such that the annular element divides the stomach (100) into two chambers, an esophagus-end chamber close to an esophagus of the patient, and a pylorus-end chamber close to a pylorus of the patient. The invention also provides a method for treatment of obesity of a patient which includes inserting an annular element having a relatively large outer boundary and a relatively small inner boundary into a stomach of the patient, and attaching the relatively large outer boundary of the annular element to an inner circumference of the stomach of the patient.

46 Claims, 9 Drawing Sheets

U.S. PATENT DOCUMENTS

| | | |
|---|---|---|
| 6,678,809 B1 | 1/2004 | Delaney et al. .............. 711/162 |
| 6,845,776 B2* | 1/2005 | Stack et al. ................. 128/898 |
| 7,025,791 B2* | 4/2006 | Levine et al. ............ 623/23.64 |
| 2004/0107004 A1 | 6/2004 | Levine et al. |
| 2004/0117031 A1* | 6/2004 | Stack et al. .............. 623/23.65 |
| 2004/0148034 A1* | 7/2004 | Kagan et al. ............ 623/23.65 |
| 2004/0220682 A1 | 11/2004 | Levine et al. |
| 2004/0249362 A1 | 12/2004 | Levine et al. |
| 2005/0149200 A1* | 7/2005 | Silverman et al. ....... 623/23.65 |

\* cited by examiner

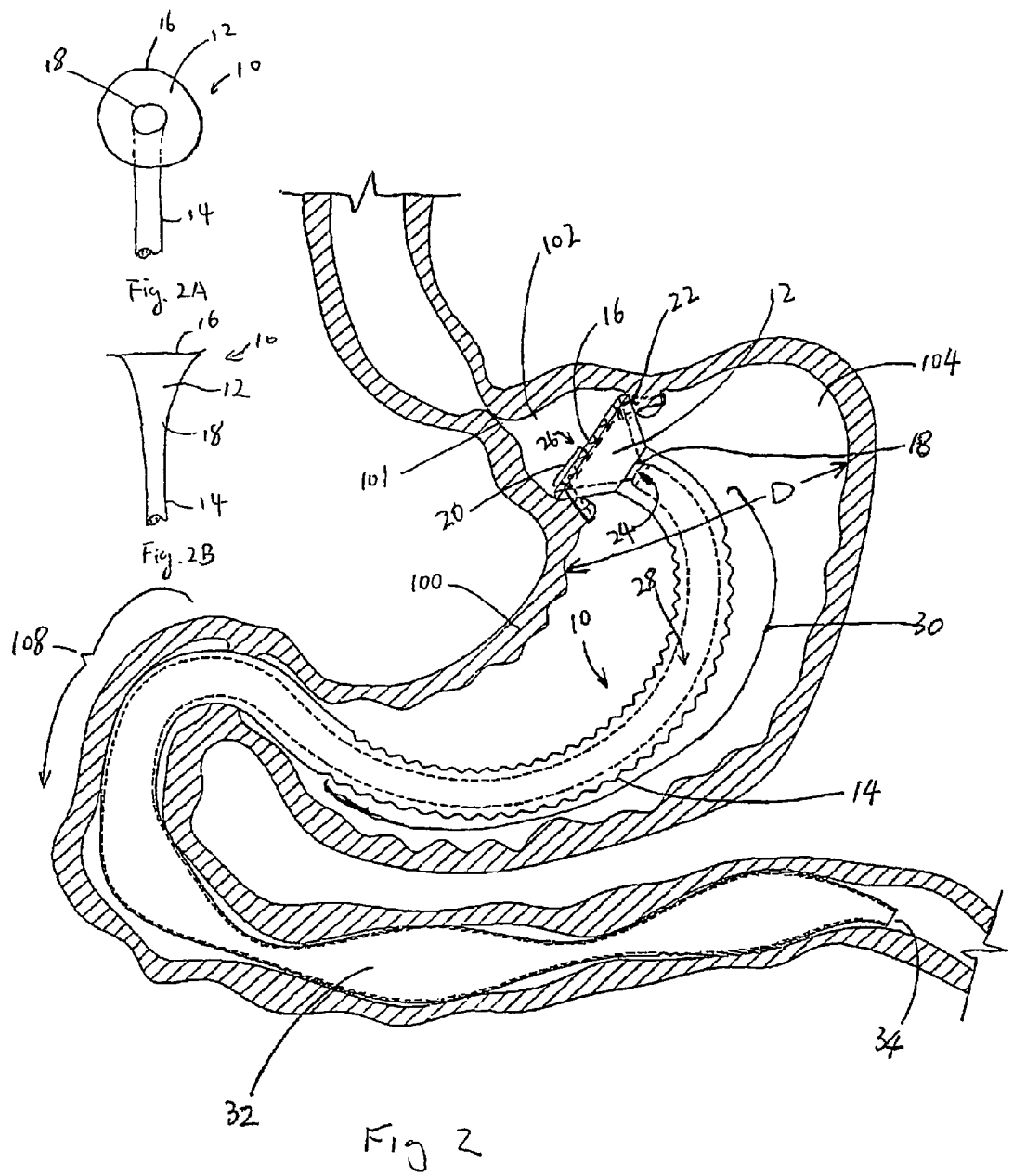

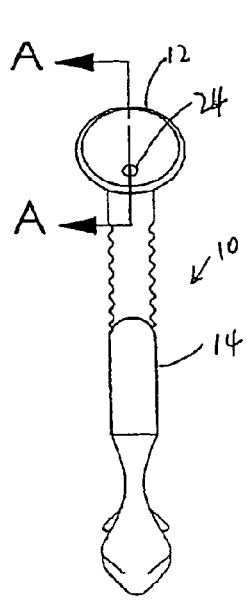
Fig. 5
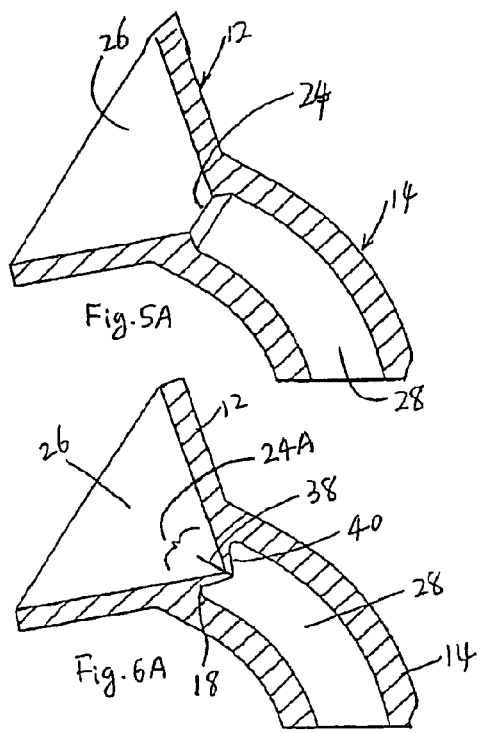
Fig. 5A
Fig. 6A
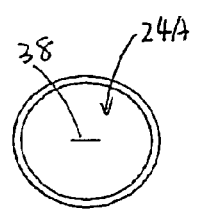
Fig. 7A
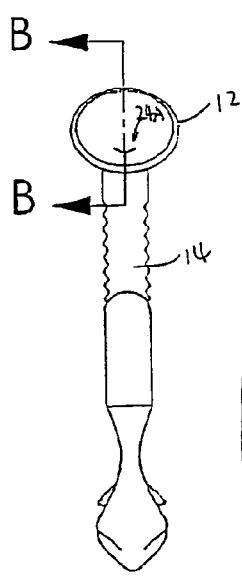
Fig. 6
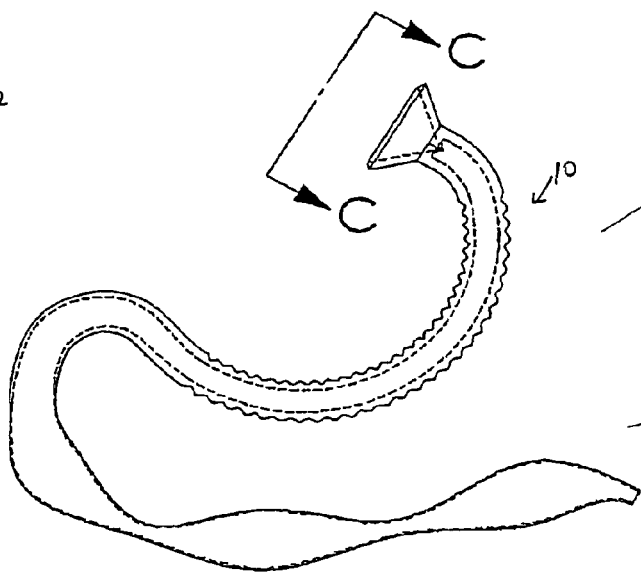
Fig. 7
Fig. 7B
Fig. 7C
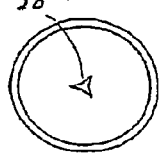
Fig. 7D

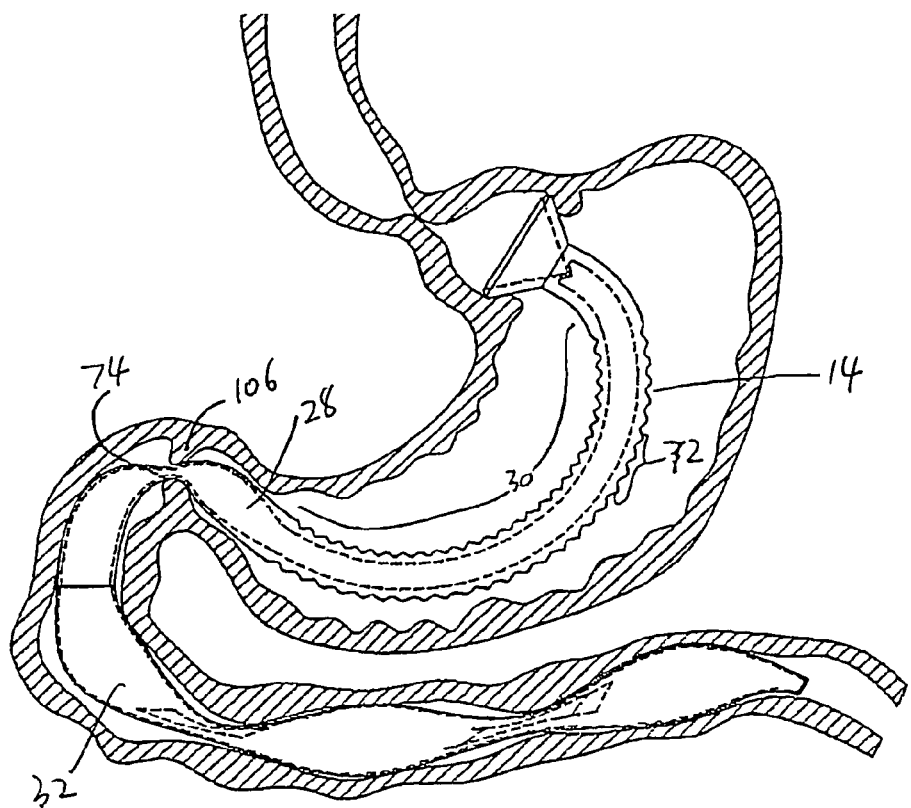
Fig. 11
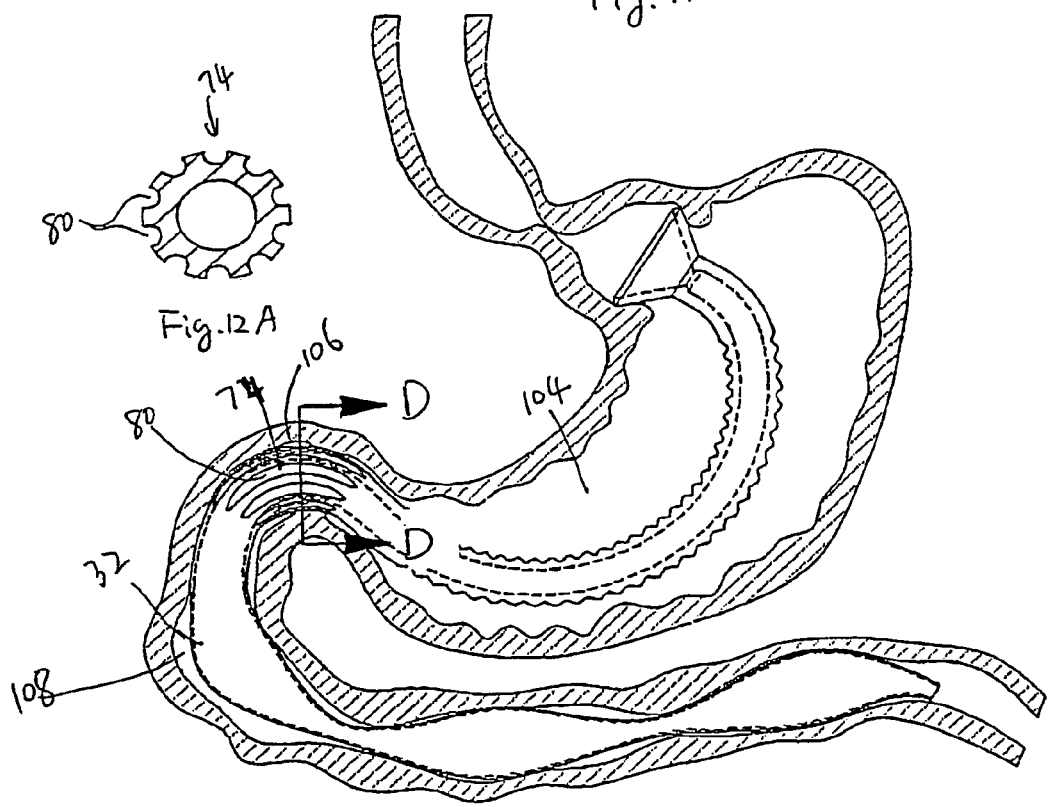
Fig. 12A
Fig. 12

GASTRIC BYPASS PROSTHESIS

FIELD OF THE INVENTION

The present invention relates to devices and methods for surgical treatment of morbid obesity, and in particular to devices and methods for gastric bypass surgery.

BACKGROUND OF THE INVENTION

Surgery for obesity accomplishes weight loss through restriction of food intake by a restrictive procedure, malabsorption of food by a malabsorptive procedure, or a combination of both restrictive and malabsorptive procedures.

The history of gastric bypass surgery for the treatment of morbid obesity is summarized in The Story of Surgery for Obesity, compiled by Alex MacGregor, MD. Many arrangements of gastric bypass have been tried in prior art. Based on success rate and a low complication rate, two procedures have risen to dominance in the field: vertical banded gastroplasty and Roux-en-y gastric bypass.

Vertical banded gastroplasty was developed by Dr. Edward E. Mason, Professor of Surgery at the University of Iowa in 1982. This technique, and its many variations, involve constricting a portion of the stomach to create a pouch exiting through a stoma using a band of synthetic material that will not stretch under the load of stomach expansion from overeating. In the Mason technique (see FIG. 1A), a portion of the stomach is stapled and a "window" created through which the band is inserted to create the stoma. A variation of this technique developed in Europe involves creation of a pouch and stoma by simply surrounding the fundus of the stomach with a band of material (see FIG. 1B). In both types of procedure, the size of the stoma is critical to the success of the procedure; too much constriction prevents food from passing, too little allows food to pass freely, defeating the purpose of the procedure. To address this condition Dr Kuzmak (Kuzmak, Yap et al. 1990) developed a band incorporating an inflatable balloon coupled to a subcutaneous access port, thereby allowing post operative adjustment of the band through injection and removal of fluid from the balloon bladder (see FIG. 1C).

Vertical banded gastroplasty is a purely restrictive procedure. Limitations and problems of vertical banded gastroplasty include the need for irreversible stomach stapling in the case of the Mason procedure and a tendency for the band to slip out of position in the European and Kuzmak procedures. All versions of vertical banded gastroplasty can be defeated if the patient consumes large quantities of sweets or highly caloric liquids (e.g. milk shakes) which pass easily through the stoma and proceed normally through the full digestive tract. This defeat mechanism has been cited as reason for a lower success rate, as measured by weight loss, for vertical banded gastroplasty in comparison to Roux-en-y gastric bypass.

Roux-en-y gastric bypass (see FIG. 1D) involves isolating (usually by stapling) a pouch in the upper stomach and forming a stoma connecting directly to the jejunum (small intestine). The isolated lower stomach and duodenum are then connected further down the jejunum, thereby keeping the biliopancreatic process intact but further down the digestive tract, thereby reducing absorption of fats. Natural peristalsis of the intestine keeps bile from migrating backwards in the digestive tract. A side effect of introducing bile further downstream of primary digestion is a condition known as Dumping. Dumping occurs when the patient eats refined sugar following gastric bypass, this causes symptoms of rapid heartbeat, nausea, tremor and fainting, sometimes followed by diarrhea. In cases where the patient needs reinforcement to discourage poor eating habits, this unpleasant side effect is a deterrent to sweets and is credited in contributing to the higher success rate of the procedure in comparison to vertical banded gastroplasty.

Roux-en-y gastric bypass is a combination restrictive/malabsorptive procedure. Limitations and problems of Roux-en-y gastric bypass include the extremely invasive, irreversible nature of reconfiguring the digestive system. Also, the anastomotic connections of the procedure are prone to stomal stenosis and obstruction.

Prior inventions of devices for the treatment of obesity have failed to provide, in combination, the three elements of Roux-en-y gastric bypass that made the procedure so successful: restriction of food intake by drastically reduced stomach volume, malabsorption from isolation of the majority of the stomach and part of the intestines from the digestive process, and the negative reinforcement of dumping syndrome that results when sugars and fat reach the jejunum without prior partial digestion.

It is an object of the present invention to induce weight loss in an obese patient through a perorally placed device that restricts food intake.

It is an object of the present invention to induce weight loss in an obese patient through a perorally placed a gastric bypass effecting device that restricts food intake and bypasses some of the absorptive regions of the GI tract thereby inducing malabsorption.

It is an object of the present invention to provide a gastric bypass effecting device and method for the treatment of morbid obesity that duplicates the functional anatomy of vertical banded gastroplasty without high surgical morbidity.

It is an object of the present invention to provide a gastric bypass effecting device and method for the treatment of morbid obesity that duplicates the functional anatomy of Roux-en-y gastric bypass without high surgical morbidity.

It is a further object of the present invention to provide a gastric bypass effecting device and method of accomplishing results comparable to Roux-en-y gastric bypass without abdominal surgery.

It is yet another object of the present invention to provide a gastric bypass effecting device that is removable, and in so doing reverses the procedure and returns the patient to his/her natural anatomy.

It is also an object of the present invention to provide a gastric bypass effecting device that facilitates attachment to the inner lumen of the stomach to form a reduced-size stomach pouch.

It is another object of the present invention to provide a gastric bypass effecting device creating stomach pouch with a precisely designed exit stoma with predicable, repeatable size and performance characteristics and does not require post-operative adjustment.

It is yet another object of the invention to provide a gastric bypass effecting device that is a food conduit bypassing the absorptive components of the upper digestive tract.

It is further an object of the invention to provide a gastric bypass effecting device that is a food conduit that works with the natural peristalsis of the digestive tract to transport material along the digestive tract.

It is also an object of the present invention to provide a gastric bypass effecting device that eliminates the risk of stomal stenosis and reduces the risk of bowel obstruction.

It is an object of the present invention to provide a gastric bypass effecting device for isolating swallowed food from a portion of the absorptive region of the GI tract while allowing stomach acid to mix with the food, thereby breaking down the food to facilitate passage through the device and the non-isolated portion of the GI tract.

It is a further object of the present invention to provide a gastric bypass effecting device and method for allowing excess stomach acid unrestricted passage from the stomach to the lower GI tract in the presence of an installed prosthetic device.

It is another object of the present invention to provide a gastric bypass effecting device and method for synchronizing the action of the stomach pouch stoma valve with that of the pyloric sphincter to facilitate the natural digestive regulatory timing and coordination.

It is yet another object of the present invention to provide a gastric bypass effecting device and method for converting the natural muscular contractions of the stomach into a pumping action within the lumen of the device to transport food contents through the lumen of the device.

It is a further object of the present invention to provide a gastric bypass effecting device and method for converting the natural muscular contractions of the stomach into a pumping action that sucks stomach acid from the pylorus-end chamber into the lumen of the device.

SUMMARY OF THE INVENTION

The forgoing objects are met in a new device and method for the treatment of morbid obesity. This new device and method achieve the restrictive aspect of vertical banded gastroplasty and roux-en-y gastric bypass through formation of a stomach pouch substantially smaller than the natural stomach. This is achieved through installation of an annular element, preferably a funnel-like shaped or conical-shaped element, which is circumferentially attached to the stomach wall dividing the stomach into two regions: the esophagus-end chamber and the pylorus-end chamber. In a preferred embodiment, the conical-shaped element is equipped with a reinforced flange extending from a proximal end of the conical-shaped element. The flange is capable of accepting sutures or staples. In one preferred embodiment, the flange is turned inward to accept the anvil element of a circular anastomotic stapler. In a preferred embodiment, the volume of the esophagus-end chamber (pouch) between the lower esophageal sphincter and the conical element is equivalent to the pouch formed in standard surgical practice for roux-en-y gastric bypass: about 30 ml to 70 ml, thus limiting the amount of food intake of a patient.

The conical-shaped element includes an interior hollow region having an opening at its distal end for passage of swallowed food into the remainder of the gastrointestinal tract (GI tract). In one embodiment, this opening is a substantially circular orifice with a diameter equivalent to the target diameter of the anastomotic stoma formed surgically in gastric bypass surgery, approximately 8 to 12 mm. In a preferred embodiment, this opening includes a valve assembly for closing the opening to prevent spontaneous passage of swallowed food or liquid until the natural digestive regulation and coordination processes trigger movement and contraction of the stomach wall in the esophagus-end chamber. The controlling of the opening is preferably accomplished by the presence of a valve that requires positive pressure differential between the proximal side of the valve and the distal side of the valve to open (for the purpose of this description, proximal shall mean closer to the mouth end of the digestive tract and distal shall mean closer to the colon end when the device is in use). Opening pressure for this stoma valve should be greater than the pressure caused by gravity on a standing column of food within the pouch (1 to 5 mmHg) and less than the continent manometric pressure of the lower esophageal sphincter (about 15 to 30 mmHg in healthy humans.) In one preferred embodiment, this valve has a higher opening pressure in the retrograde direction than in the forward direction to reduce the incidence of reflux into the esophagus. In another preferred embodiment, the stoma valve employs a valve with hysteresis such that the valve opens fully at an initial cracking pressure and closes fully at a closing pressure lower than the cracking pressure, thereby offering more complete emptying of the pouch with smaller stomach wall contraction pressures. In another preferred embodiment, the pouch stoma valve communicates with the pyloric sphincter such that the stoma valve opens upon relaxation of the pyloric sphincter muscle and closes in sync with pyloric sphincter muscle pressure.

In another preferred embodiment, further elements are added to provide a malabsorptive aspect to the device. In one embodiment, the malabsorptive aspect is achieved by providing an elongated flexible tube extending from the distal end of the conical-shaped element to a distal end. The elongated flexible tube has a length so that the tube passes the pylorus of the patient and the distal end is positioned in the intestine when the device is in use. The elongated flexible tube defines an inner central lumen which establishes communication between the distal stoma orifice or the valve of the conical-shaped element and the intestines distal to the pylorus, but not in communication with the pylorus-end chamber between the distal side of the conical-shaped element and the pyloric sphincter, thereby isolating this otherwise absorptive stomach region from contact with food. In one preferred embodiment, the tube is made of a flexible material such that the natural muscular movement of the stomach creates a pumping action to the tube to assist in transporting food through the lumen. In one preferred embodiment, the portion of the lumen transiting the pyloric sphincter has sufficient diametric rigidity to resist collapse from pyloric sphincter pressure. In other embodiments, particularly the embodiment without a stoma valve at the distal end of the conical-shaped element, the region transiting the pyloric sphincter is sufficiently pliable to allow the tube to collapse and the lumen to be closed under pyloric sphincter pressure.

In one embodiment, the diameter of the flexible tube is sized to provide a space between the outer surface of the tube and the circumference of the pylorus when the sphincter is in a relaxed state, to allow passage of any excess stomach acid that may have accumulated in the pylorus-end chamber. In other embodiments, passageways are provided on the outer surface of the flexible tube, for example, grooves defined on the outer surface of the tube, to allow passage of the stomach acid when the pyloric sphincter is in the closed state. In another preferred embodiment, passageways are provided to allow stomach acid to pass one-way from the pylorus-end chamber into the inside of the lumen to assist in breakdown of food within the lumen.

In one preferred embodiment, the elongated flexible tube extends beyond the pylorus and ends in the upper duodenum. In another preferred embodiment, the elongated flexible tube transits a portion of the duodenum, which portion has a length equivalent to the length of the portion of the duodenum bypassed in standard practice of a roux-en-y gastric bypass surgery (approximately 50 to 200 cm), thereby rendering this portion of the intestine malabsorptive. In a further preferred embodiment, the elongated flexible tube includes at least a portion that is collapsible under peristaltic pressure from the stomach or the intestinal wall, thereby allowing food to be transported through the lumen by means of stomach or intestinal peristalsis. In another preferred embodiment, the collapsible portion starts from the proximal end of the duodenum to the distal end of the tube. In one preferred embodiment, the portion of the tube in the duodenum region is constructed such that it is in a naturally collapsed state, such as a flattened tube, with no external pressure required to compress the tube closed. In another preferred embodiment, the tube is constructed such that the inner central lumen is in a naturally open state, such as a round tube, such that external pressure is required to pinch the lumen closed and the lumen returns to the open state when external pressure is removed. In another preferred embodiment, a portion of the tube which is disposed in the peristaltic portion of the duodenum when the device is in use is made of an elastic material. The portion of the tube may be compressed by the peristalsis of the duodenum and the elastic wall of the tube forces tube to return to its naturally open state when the pressure from the duodenum peristalsis is removed, thereby creating a negative pressure within the lumen to assist in propulsion of food in the distal direction and to assist in sucking stomach acid into the inside of the lumen through the one-way acid valve, if provided.

The most preferred embodiment of the present invention will be designed for peroral implantation and explantation. In one preferred embodiment, the implantation will be performed as follows:

Preparation: An endoscopic suturing device such as the C. R. BARD ENDOCINCH™, or other endoscopic suturing device known to the art, will be used to place a plurality of sutures (10 to 12 sutures in a preferred embodiment) in the gastric cardiac region in a ring approximately 3 cm distal to the gastroesophageal junction. The sutures will be 2 m long polypropylene monofilament placed in a mattress configuration with a felt pledget. The suture tails, in pairs, will be passed through the circumference of the gastric bypass prosthesis (GBP) attachment ring flange using a free needle. A system of cut-away tubes (i.e. drinking straws) may be used to organize the strands and prevent suture pair entanglement.

Introduction: Suture pairs exiting the GBP flange will be taped together and identified by location. Each of the 10 to 12 pairs will be passed through the lumen of a 20 mm diameter hollow introducer tube. The GBP will be lubricated with hydrogel and stuffed in the distal end of the introducer tube (Cut-away organized tubes, if used, will be removed at this time.) The tube containing the GBP will be slid along the suture strand pairs in the same manner as an artificial heart valve is "parachuted" into place.

Deployment: Once the introducer tube clears the gastroesophageal sphincter, the GBP is ejected into the stomach by gently pushing from the distal end of the tube with a plastic rod. The suture pairs are cinched up to take up slack around half the diameter of the flange, but leaving a gap big enough for a 12 mm endoscope on one side. With the introducer tube withdrawn but the suture tails still in the esophagus, a 12 mm steerable endoscope is introduced through the esophagus and through the gap left at the edge of the GBP flange. The distal end of the GBP is visualized and captured using a grasper introduced through the endoscope instrument canal. The endoscope, with the distal end of the GBP attached, is maneuvered through the pyloric sphincter and the duodenum to the full length of the GBP where the distal end is released and the endoscope withdrawn.

Fixation: The endoscope is repositioned just proximal of the GBP attachment ring flange. The suture pairs are cinched up, closing off the gap formerly used by the endoscope. One by one, each pair of suture tails is tied with a sliding lock-knot (Dines knot, Roeder knot, etc.) facilitated by a knot-pusher to complete the 10 to 12 mattress stitches. The flange is then inspected via endoscope, and the suture tails are trimmed using micro-scissors through the endoscope instrument canal, and the endoscope removed. In other preferred embodiments, a circular anastomotic stapler such as the ETHICON PROXIMATE™ is used in place of suturing.

Explantation: This step entails endoscopic visualization of the GBP attachment flange, snipping the sutures at one side of the knot, and plucking the sutures out by the knot. The introducer tube, lubricated inside, is inserted past the gastroesophageal sphincter. A bent-wire hook is used to firmly engage one side of the attachment flange under endoscope visualization and pull it into the distal end of the introducer tube. When the wide flange portion of the GBP is fully enclosed by the introducer tube, the tube and GBP implant are pulled free of the GI tract as an assembly.

Other objects, features and advantages will be apparent from the following detailed description of the preferred embodiments thereof taken in conjunction with the accompanying drawings in which:

BRIEF DESCRIPTION OF THE DRAWINGS

FIG. 2 is a schematic view of the gastric bypass prosthesis installed in the stomach and upper intestinal tract;

FIG. 2A is a schematic view of a preferred embodiment of the gastric bypass prosthesis in accordance with the present invention;

FIG. 2B is a schematic view of a preferred embodiment of the gastric bypass prosthesis in accordance with the present invention;

FIG. 5 is a side view of a preferred embodiment of the gastric bypass prosthesis with an orifice stoma;

FIG. 5A is a cross-sectional view of a proximal end of the preferred embodiment of the gastric bypass prosthesis with an orifice stoma shown in FIG. 5, taken along line A-A;

FIG. 6 is a side view of a preferred embodiment of the gastric bypass prosthesis with a check valve stoma;

FIG. 6A is a cross-sectional view of a proximal end of the preferred embodiment of the gastric bypass prosthesis with a check valve stoma shown in FIG. 6, taken along line B-B;

FIG. 7 is a schematic view of a preferred embodiment of the gastric bypass prosthesis with a check valve stoma;

FIG. 7A is an enlarged view of a proximal end of a preferred embodiment of the gastric bypass prosthesis with a check valve stoma with a single slit in a closed condition, viewed from arrows C-C in FIG. 7;

FIG. 7B is an enlarged view of a proximal end of a preferred embodiment of the gastric bypass prosthesis with a check valve stoma with a single slit in an open condition, viewed from arrows C-C in FIG. 7;

FIG. 7C is an enlarged view of a proximal end of a preferred embodiment of the gastric bypass prosthesis with a check valve stoma with a plurality of slits in a closed condition, viewed from arrows C-C in FIG. 7;

FIG. 7D is an enlarged view of a proximal end of a preferred embodiment of the gastric bypass prosthesis with a check valve stoma with a plurality of slits in an open condition viewed from arrows C-C in FIG. 7;

FIG. 11 is a schematic view of a gastric bypass prosthesis installed in the stomach with a trans-pyloric section collapsible by pyloric sphincter pressure in accordance with a preferred embodiment of the present invention;

FIG. 12 is a schematic view of a preferred embodiment of the gastric bypass prosthesis installed in the stomach with a trans-pyloric section with grooves to permit passage of stomach acid;

FIG. 12A is a cross-sectional view of the tube of the preferred embodiment shown in FIG. 12, taken along line D-D;

DETAILED DESCRIPTION OF PREFERRED EMBODIMENTS

Figure 1A:
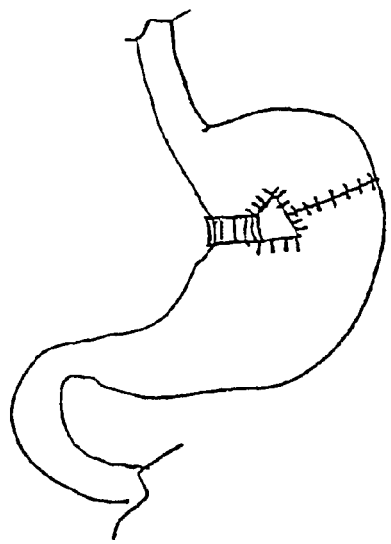
FIG. 1A is a prior art diagram of a vertical banded gastroplasty a la Mason.
Figure 1B:
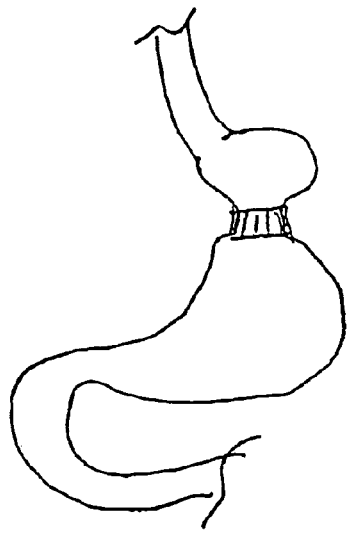
FIG. 1B is a prior art vertical banded gastroplasty without inflatable balloon.
Figure 1C:
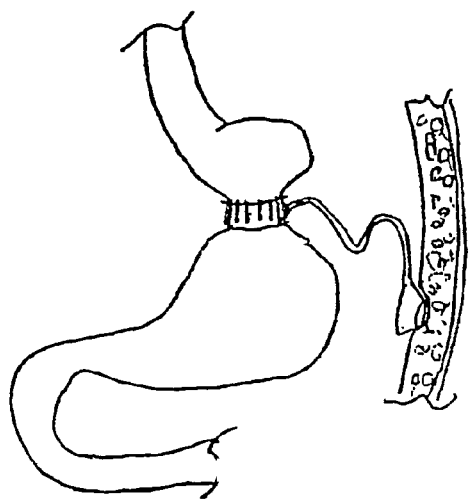
FIG. 1C is a prior art vertical banded gastroplasty with stomal dilation controlling balloon a la Kuzmak.
Figure 1D:
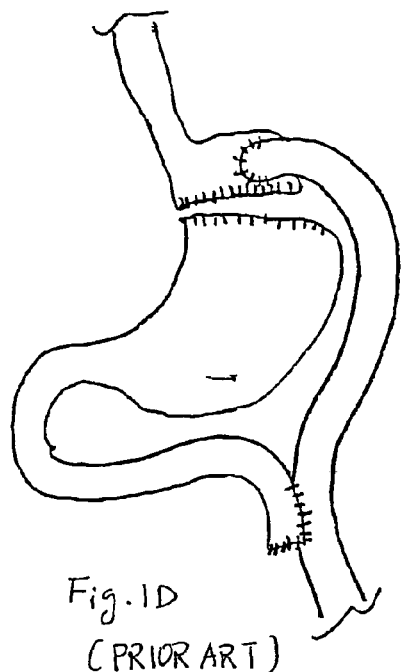
FIG. 1D is a prior art diagram of the Roux-en-y gastric bypass.

For the purposes of promoting an understanding of the present invention, reference will now be made to the embodiments illustrated in the drawings and specific language will be used to describe the same.

FIG. 2 shows a preferred embodiment of a gastric bypass prosthesis in accordance with the present invention. As shown in FIG. 2, the gastric bypass prosthesis 10, which is disposed in a stomach 100, includes a substantially annular element 12 and an elongated tubular element 14. In other preferred embodiments, as shown in FIGS. 2, 2A, and 2B, the annular element 12 may be flat (FIG. 2A), substantially conical-shaped, funnel-shaped, or trumpet-shaped (FIG. 2B). The element 12 also can be constructed with other shapes suitable for attaching to the stomach lining. The element 12 is preferably made of a flexible material, but also can be made of rigid or semi-rigid materials. In one preferred embodiment, the annular element 12 may be flat-shaped and made of a flexible material, and when in use or under load, the annular element 12 may extend to a conical shape. The annular element 12 includes a relatively large outer boundary 16 and a relatively small inner boundary 18. The elongated tubular element 14 extends from the relatively small inner boundary 18 of the annular element 12. FIG. 2 shows an annular element 12 with a substantially conical shape which includes a relatively large proximal end 16 (relatively large outer boundary) and a relatively small distal end 18 (relatively small inner boundary) (for the purpose of this description, proximal shall mean closer to the mouth end of the digestive tract and distal shall mean closer to the colon end when the device is in use). The elongated tubular element 14 extends from the relatively small distal end 18 of the conical shaped element 12. The conical-shaped element 12 and the tubular element 14 are preferably made of a biologically compatible, flexible material that is impervious to digestive fluids. In one preferred embodiment, the tubular element 14 are made entirely of silicone rubber. The conical-shaped element 12 may be made of the same material as the tubular element 14 or other suitable materials, and may be made integrally with the tubular element 14.

The relatively large proximal end 16 of the conical-shaped element 12 further includes an annular flange 20 extending from the rim of the proximal end 16 for attaching the proximal end 16 to the stomach lining by suture 22, or staples, adhesive, a combination of these, or other suitable means. In one embodiment, the flange 20 is made of the same material as the remainder of the device (e.g. silicone rubber). In one preferred embodiment, the flange 20 includes a reinforcing fibrous woven or felt-like material to resist tearing. In another preferred embodiment, the relatively small distal end 18 of the funnel-shaped element 12 defines an opening 24 that functions as a valve or stoma connecting an interior region 26 of the funnel-shaped element 12 to an internal lumen 28 defined within the tubular element 14. In one embodiment, this opening 24 is a substantially circular orifice with a diameter equivalent to the target diameter of the anastomotic stoma formed surgically in gastric bypass surgery, approximately 8 to 12 mm. The funnel-shaped element 12 when attached to the lining of the stomach 100, divides the stomach 100 to a proximal esophagus-end chamber 102 and a distal pylorus-end chamber 104. As shown in FIG. 2, the stomach has an increasing cross section and a decreasing cross section. The flange 20 of the funnel-shaped element 12 is preferably attached to the inner wall of the increasing section of the stomach. In another preferred embodiment, the funnel-shaped element 12 is attached to the stomach near the esophagus opening 101. In a preferred embodiment, the volume of the esophagus-end chamber (pouch) 102 between the lower esophageal opening 101 and the conical element 12 is equivalent to the pouch formed in standard surgical practice for roux-en-y gastric bypass: about 30 ml to 70 ml, thus limiting the amount of food intake by a patient at one time. In a preferred embodiment, the proximal end 16 of the conical-shaped element 12 has a diameter which is smaller than the diameter D of a portion of the stomach where the conical-shaped element 12 is to be attached, such that when the conical-shaped element 12 is attached to the inner wall of the portion, the portion of the stomach is constricted.

Figure 3:
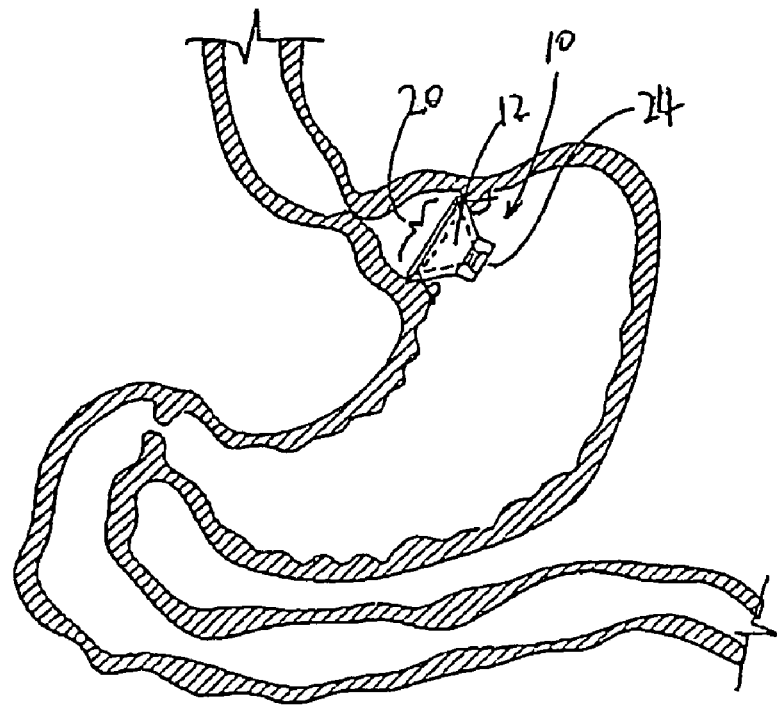
FIG. 3 is a schematic view of a preferred embodiment of the gastric bypass prosthesis installed in the stomach and upper intestinal tract.
Figure 4:
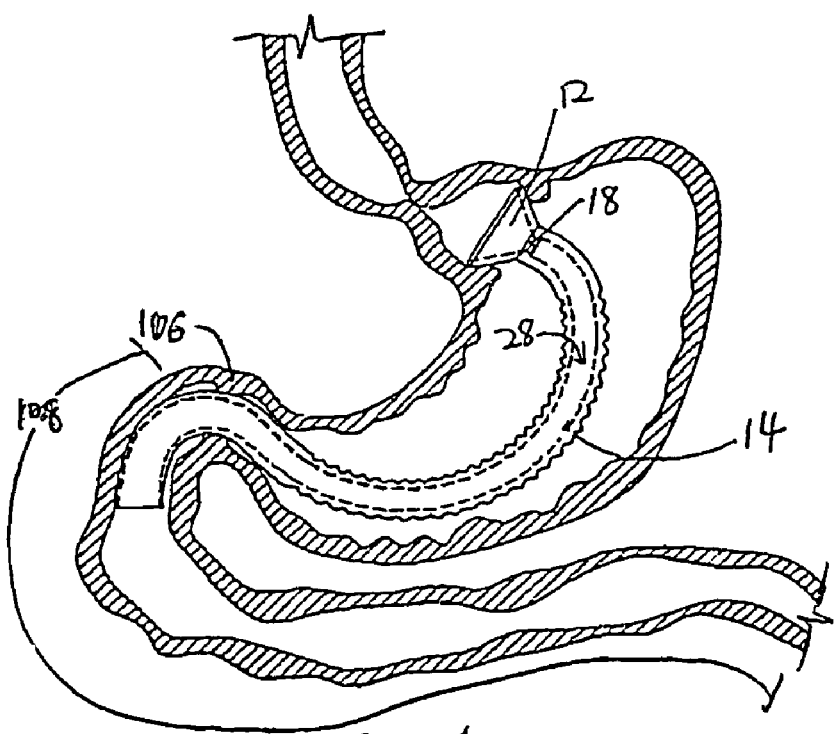
FIG. 4 is a schematic view of a preferred embodiment of the gastric bypass prosthesis installed in the stomach and upper intestinal tract.

The length of the tubular element 14 may vary in accordance with the need of a patient. In one preferred embodiment, as shown in FIG. 3, the device 10 includes only the funnel-shaped element 12 which includes the flange 20 and the stoma 24. FIG. 4 shows another preferred embodiment which further comprises a flexible tubular element 14 extending from the distal end 18 of the funnel-shaped element 12 passing the pyloric sphincter 106 to the duodenum 108. The inner lumen 28 of the flexible tubular element 14 is preferably maintained open and un-constricted. In other embodiments, the flexible tubular element 14 may be short and extend within the stomach 100. In a preferred embodiment, the elongated tubular element 14 has a length of about 50 to 200 cm.

In still another preferred embodiment, as shown in FIG. 2, the tubular element 14 includes two connected sections, a first open tube section 30 in which the inner lumen 28 is preferably maintained open, and a second thin-walled tube section 32 which is preferably a thin-walled tube that is able to be collapsed with minimal pressure from the outside. In one alternate embodiment, this thin-walled section 32 is naturally in a collapsed state and is opened only by pressure from inside the tube 32. In another embodiment, the thin-walled tube section 32 extends the full length of the tubular element 14 from the distal end 18 of the funnel-shaped element 12 to a distal end 34 of the tubular element 14. In yet another embodiment, the tubular element 14 may include only the open tube section 30 which extends from the distal end 18 of the funnel-shaped element 12 to the distal end 34 of the tubular element 14. In a preferred embodiment, the distal end 34 of the tubular element 14 ends in an opening. In other embodiments, the distal end 34 is closed and perforations are provided in the walls of the tubular element 14 near the distal end 34.

In the preferred embodiments in which the tubular element 14 includes a portion or a section which may collapse under pressure, the wall of such portion or section is preferably made of a flexible material that collapses when under a pressure differential of about 0 to 20 mmHg between the outside of the tubular element 14 and the inside of the tubular element 14. In these embodiments, the remainder of the tubular element 14 (portions other than the above-described collapsible portion) may collapse under a pressure differential greater than 20 mmHg between the outside of the tubular element 14 and the inside of the tubular element 14.

FIG. 5 is a schematic view of one preferred embodiment and 5A is a cross-sectional view of the embodiment taken along line A-A in FIG. 5. As shown in FIGS. 5 and 5A, the device 10 includes a simple orifice restriction stoma 24 which connects the interior region 26 of the funnel-shaped element 12 with the inner lumen 28 of the tubular element 14.

FIGS. 6 and 6A show another preferred embodiment of the device 10, in which the device 10 further includes a valve assembly 24A disposed at the opening 24. The valve assembly 24A is constructed as a stoma valve comprising a slit 38 defined in a circular member 40, preferably a thin conical section or a circular pad made of a flexible material. The thin conical section 40 extends from the distal end 18 of the funnel-shaped element 12, and is preferably constructed integrally with the funnel-shaped element 12. The valve 24A preferably opens when the pressure differential between the pressure in the interior region 26 which is on the proximal side of the valve 24A and the pressure in the lumen 28 which is on the distal side of the valve 24A reaches a desired value. A pressure gradient in the reverse direction (from the distal side of the valve 24A to the proximal side of the valve 24A) would hold the valve closed in all but extraordinary biological pressure conditions. The desired pressure differential for opening the valve 24A is controlled by the design, size, and position of the valve 24A, the thickness of the wall of the conical section 40, and the hardness of the material used in funnel-shaped element 12 and the conical section 40.

FIG. 7 is a side schematic view of the embodiment 10 shown in FIG. 6 and 6A. FIGS. 7A-7D show various embodiments of the valve 24A viewed from arrows C-C. FIG. 7A shows a single slit valve in the closed condition. FIG. 7B shows a single slit valve as it would appear when forced open by gastric constriction pressure within the pouch 102. FIG. 7C shows a stoma valve with a plurality of slits 38 in closed condition, and FIG. 7D shows the slits 38 are in open condition. The valve assembly 24A may be constructed with a thin flat section attached to the distal end 18, instead of the conical-shaped section 40. Other embodiments of the invention may employ other pressure responsive valves and check valves, numerous examples of which are known to the art. The arrangement of the opening 24 and the valve assembly 24A shown in FIGS. 5-7D makes the opening 24 to function as a stoma orifice.

Figure 8A:
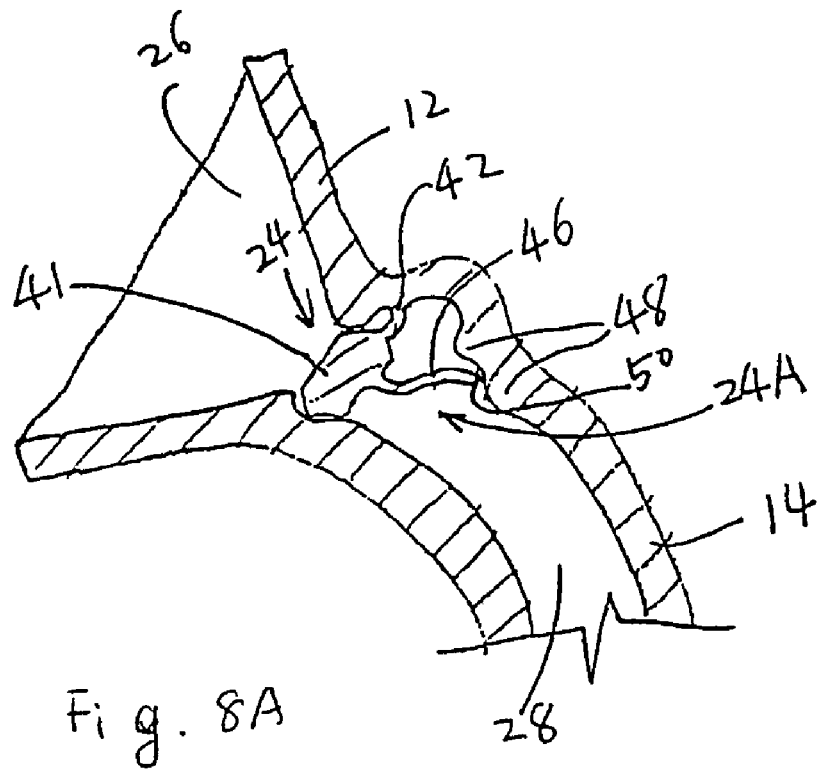
FIG. 8A is a cross-sectional view of a preferred embodiment of the proximal end of the gastric bypass prosthesis with a check valve stoma with hysteresis in a closed condition.
Figure 8B:
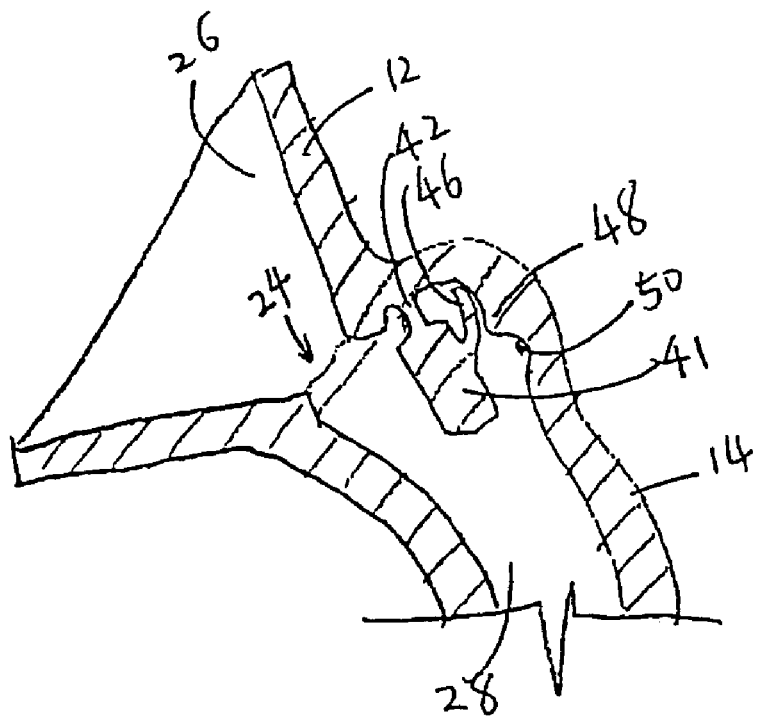
FIG. 8B is a cross-sectional view of a preferred embodiment of the proximal end of the gastric bypass prosthesis with a check valve stoma with hysteresis in an open condition.

FIG. 8A shows a preferred stoma valve arrangement with built-in hysteresis. In this embodiment, the valve assembly 24A includes a plug element 41, which is sized to engage with and close the opening 24 and connected to an elastic hinge element 42, which extends inwardly from an inner surface of the tubular element 14. A small flexible protrusion 46 extends from a distal side of the plug element 41 toward a distal end. A small bump 48 extends inwardly from the inner surface of the tubular element 14 near the proximal end of the tubular element 14. In a preferred embodiment, a small socket 50 is defined in the middle of the small bump 48. The distal end of the small protrusion 46 rests in the socket 50 when the plug element 40 closes the opening 24, as shown in FIG. 8A. Sufficient pressure to open the valve assembly 24A causes the plug element 41 to swing down to a lower energy state, which in turn causes the protrusion 46 to snap over the rim of the bump 48 to an upper position as shown in FIG. 8B. The protrusion 46 provides resistance at initial opening, thereby achieving hysteresis. The valve assembly remains open until the pressure differential reduced to a predetermined lower value, for example zero. When the pressure differential reduced to the predetermined lower value, the elastic hinge element 42 biases the plug element 40 toward the closed position and the flexible protrusion 46 to return to the position where the distal end of the protrusion rests in the socket 50. The device also can use other suitable hysteresis or snap-action mechanisms which are know in the art to control the opening and closing of the valve assembly 24A.

Figure 9A:
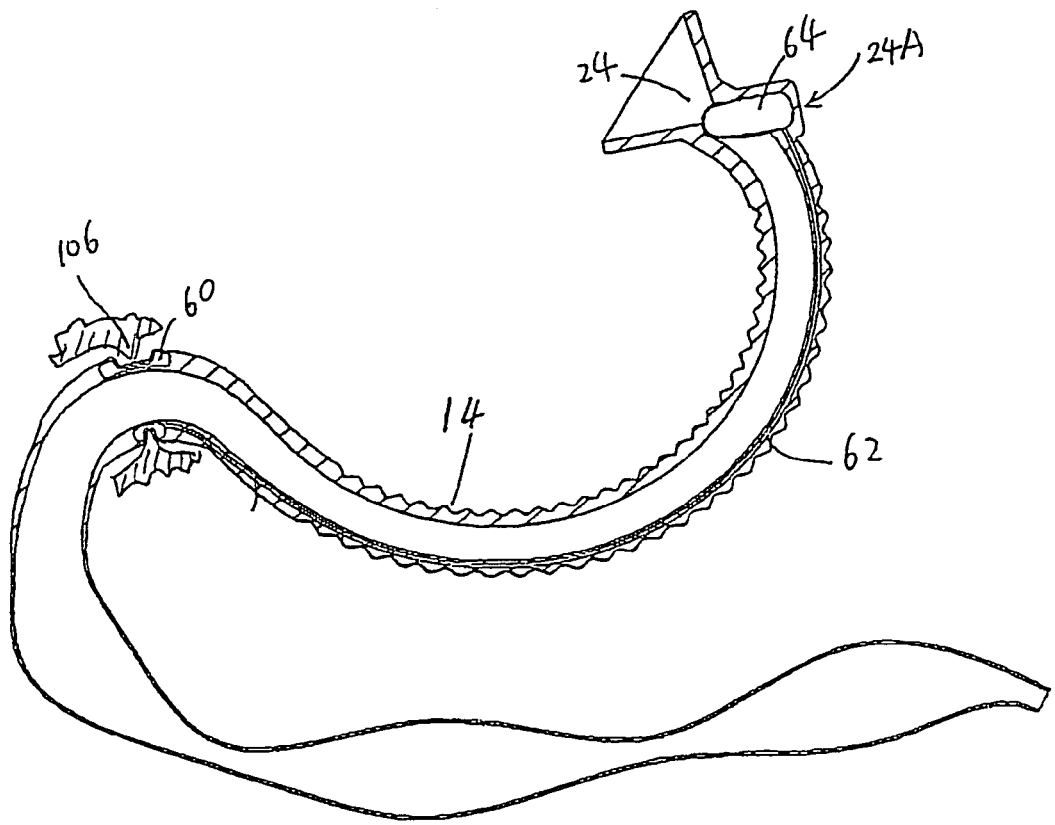
FIG. 9A is a cross-sectional view of a preferred embodiment of the gastric bypass prosthesis with a stoma valve controlled by the action of the pyloric sphincter, with the valve in a closed condition.
Figure 9B:
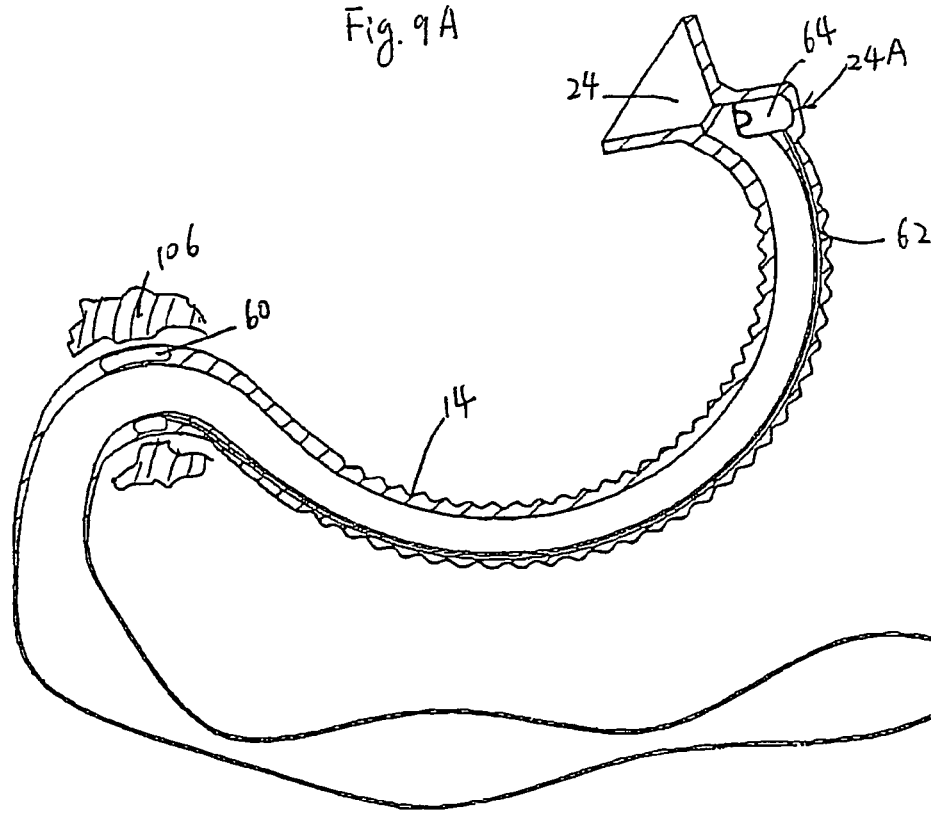
FIG. 9B is a cross-sectional view of a preferred embodiment of the gastric bypass prosthesis with a stoma valve controlled by the action of the pyloric sphincter, with the valve in the open condition.

FIGS. 9A and 9B show a gastric bypass prosthesis with a stoma valve assembly 24A controlled by the action of the pyloric sphincter 106. An annular fluid filled chamber 60 is defined within the tubular element 14 in the region where the device 10 passes through the pyloric sphincter 106. A balloon-like bulb 64 is deployed at the stoma opening 24. The balloon-like bulb 64 is sized to close the opening 24 when the bulb 64 is inflated. A passageway 62 is provided for providing a fluid communication between the chamber 60 and an inner chamber of the balloon-like bulb 64. Pressure from the pyloric sphincter 106 collapses the chamber 60, thereby forcing the fluid through the passageway 62 to the balloon-like bulb 64 at the stoma opening 24, inflating the balloon-like bulb 64 which in turn closes the stoma opening 24. FIG. 9B shows the pyloric sphincter 106 in a relaxed condition, as it would be when the timing of the digestive process calls for emptying of the stomach contents into the intestines. At this time, the pressure from the pyloric sphincter 106 is removed from the annular chamber 60, and the annular chamber 60 expands, drawing fluid from the inner chamber of the balloon-like bulb 64 through the passageway 62 to the chamber 60, causing the balloon-like bulb 64 to retract, and thereby opening the stoma opening 24. Other embodiments employing other means may be used to achieve the same coordination of the stoma valve assembly 24A and the pyloric sphincter 106, such as mechanical linkages, electrically actuated mechanisms and microelectronic pressure sensors signaling remote action through electrical or fiber-optic signals, or any other remote actuation means known to the art. Still other embodiments can be used to trigger stoma valve action based on signals from microelectronic measurements which detects the presence of digestive juices and hormones used by the body to time and regulate the digestive process.

Figure 10:
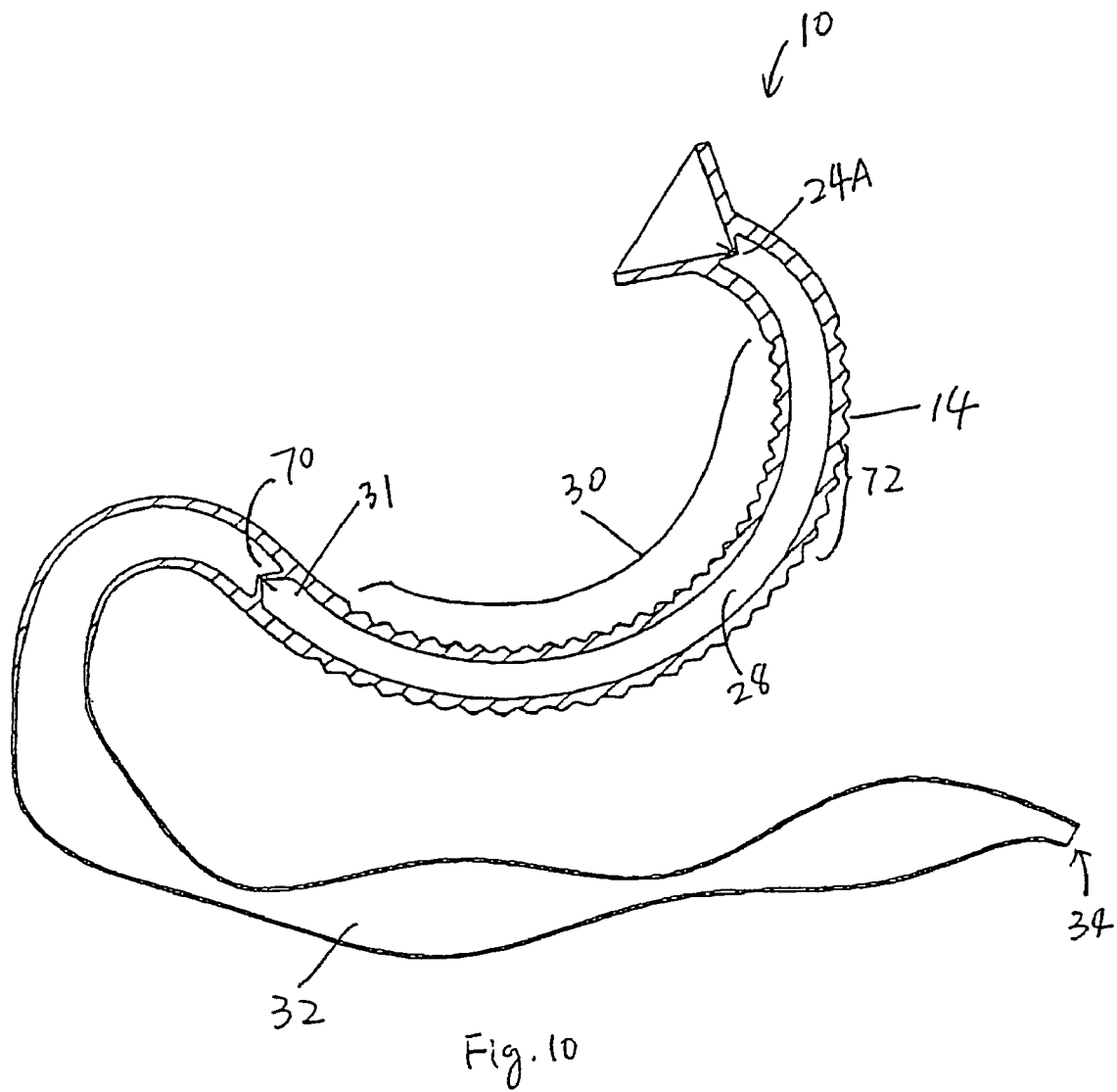
FIG. 10 is a cross-sectional view of another preferred embodiment of the gastric bypass prosthesis in accordance with the present invention.

FIG. 10 shows another preferred embodiment where a second one-way check valve 70 is used at a distal end 31 of the open tube section 30 of the tubular element 14 in addition to the stoma valve 24A which is disposed at the proximal end of the tubular element 14. Additionally, the wall of the open tube section 30 is preferably constructed with a plurality of pleats 72 such that the length of the section 30 compresses and expands without substantial change to the lumen diameter of the inner lumen 28, like an accordion, when subjected to the natural contractions and churning action of the stomach wall. This results in a pumping action that helps propel swallowed food through the device 10.

In the above-described embodiments as shown in FIGS. 5-10, the valve assembly 24A is preferably constructed such that opening pressure for this valve assembly 24A is greater than the pressure caused by gravity on a standing column of food within the pouch (1 to 5 mmHg) and less than the continent manometric pressure of the lower esophageal sphincter (about 15 to 30 mmHg in healthy humans.). In a preferred embodiment, the pressure assembly 24A opens when the pressure differential from the proximal side of the opening 24 to the distal side of the opening 24 is equal to or greater than the pressure differential created by swallowing. In the embodiment with hysteresis means, the pressure differential for opening the valve assembly 24A is also preferably approximate to the pressure differential created by swallowing, and the lower pressure differential for closing is preferably approximate to the normal pressure in the stomach. In another preferred embodiment, the valve assembly 24A opens when pressure differential is greater than about zero, in another preferred embodiment, about 20 mmHg. It is also preferable that the valve 24A is a one-way valve assembly, allowing food passage from the proximal side to the distal side of the opening, and remain closed when the pressure on the distal side is greater than the proximal side of the opening 24, thus preventing reflex of the food.

In another preferred embodiment, as shown in FIG. 11, the tubular element 14 includes a trans-pyloric section 74 which is disposed at the pylorus 106. The lateral wall of the section 74 transiting the pylorus is preferably flexible enough such that the lumen 28 with the section 74 is squeezed shut by the pyloric sphincter when the pyloric sphincter closes the pylorus 106. This embodiment, which may also includes the flexible tube section 30 with a plurality of accordion-like pleats 72, can have a pumping action similar to that shown in FIG. 10 and can allow food movement in concert with the regulatory digestive timing of the body similar to the embodiment shown in FIGS. 9A and 9B.

FIG. 12 shows another preferred embodiment designed to prevent build-up of excess stomach acid in the pylorus-end chamber 104. In this embodiment, as best shown in FIG. 12A, the trans-pyloric portion 74 of the device 10 which transits the pylorus 106 is provided with a plurality of open-faced fluted channels or grooves 80 on the outer surface of the section 74. The channels 80 preferably run parallel to the axis of the device 10 such that when the pyloric sphincter 106 is closed, excess acid can freely pass into the intestines 108 through the channels 80. Other alternate embodiments employing enclosed channels isolated from the interior lumen 28 of the device 10 with openings in the pylorus-end chamber 104 and the intestines 108 can be used. Other alternate embodiments can employ a single passageway or flute at the section 74. Still other alternate embodiments may use single or multiple passageways or flutes in non-parallel or serpentine geometry.

Figure 13A:
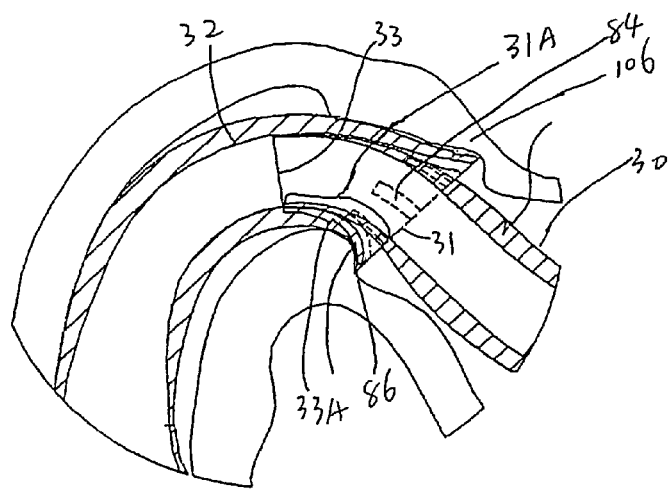
FIG. 13A is a cross-sectional view of the trans-pyloric section of the preferred embodiment shown in FIG. 13, taken along arrows E-E.
Figure 13:
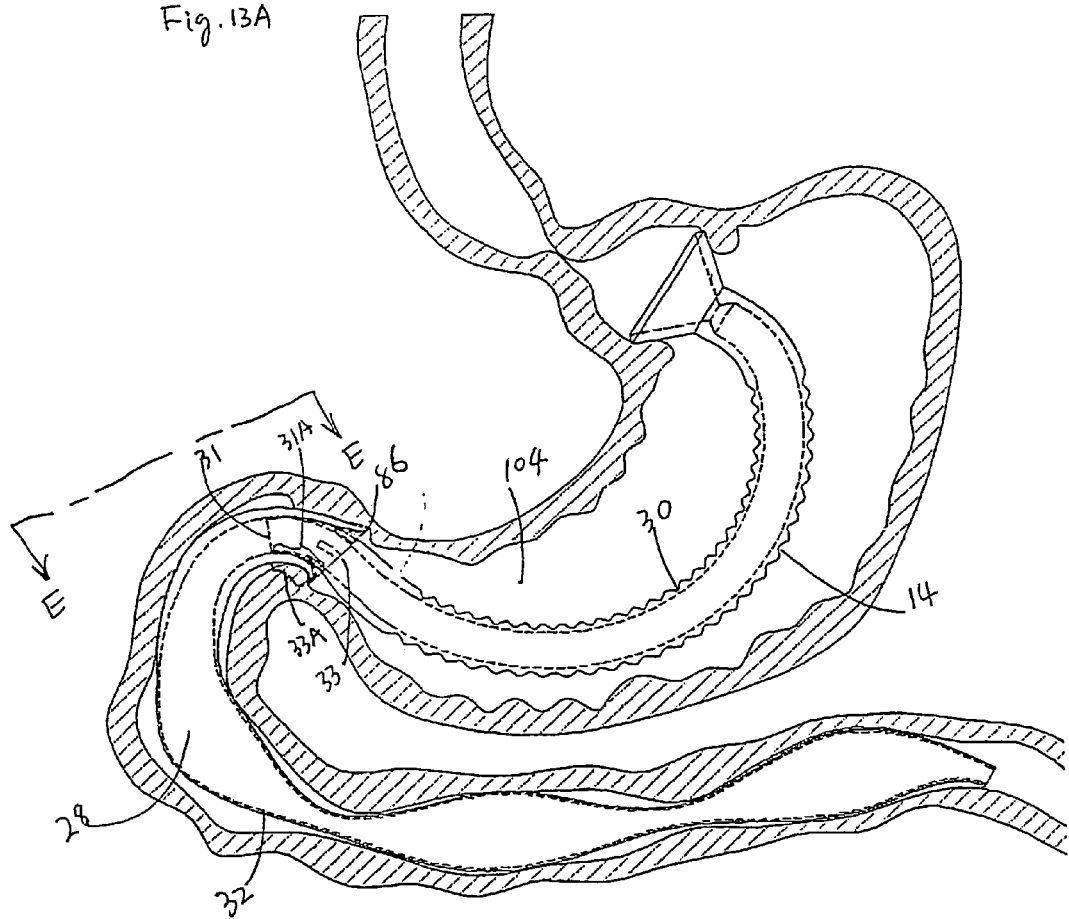
FIG. 13 is a schematic view of a preferred embodiment of the gastric bypass prosthesis installed in the stomach with a trans-pyloric section designed to introduce stomach acid into the lumen without allowing food to escape.

FIG. 13 shows a preferred embodiment designed to allow introduction of stomach acid into the lumen 28 of the device to aid in breakdown of the swallowed food, while still keeping the food inside the lumen 28 and isolated from the proximal portion of the digestive system. In the preferred embodiment, the tubular element 14 includes two sections, a first section 30 and a second section 32. The first section 30 includes a distal portion 3 1A whose outer diameter tapers to a distal end 31 or the lateral wall of the distal portion 31A thins to its distal end 31. The second section 32 includes a proximal portion 33A which is preferably trumpet-bell shaped and includes a proximal end 33 defining an opening having an inner diameter greater than the outer diameter of the distal end 31 of the first section 30. The two sections 30 and 32 are connected by inserting the distal portion 31A of the first section 30 into the proximal portion 33A of the second section 32, such that the two sections 30 and 32 form the continuous inner lumen 28 extending within the two sections 30 and 32. The first section 30 is preferably flexible and round shaped such that the portion of the inner lumen 28 within the section 30 is maintained open. The second section 32 is preferably thin-walled and made of a flexible material that can be collapsed with minimal pressure from the outside. In one alternate embodiment, this thin-walled section 32 is naturally in a collapsed state and is opened only by pressure from inside the section 32.

As shown in FIG. 13A, the distal portion 31A of the first section 30 is inserted into and overlaps with the proximal portion 33A of the second portion 32, forming an overlapping portion. When the pressure inside the lumen 28 of distal portion 31A is greater than the pressure within the pylorus-end chamber 104, the thin lateral wall of the distal portion 31A expands that results in the outer surface of the distal portion 31A of the first section 30 in tight contact with the inner surface of the proximal portion 33A of the second section, sealing the overlapping junction between two tube sections 30 and 32 and keeping the contents of the lumen 28 isolated from the digestive system. When the pylorus 106 exerts pressure to the overlapping portion, the thin-walled distal portion 31A collapses inwardly and disparts from the proximal portion 33A of the second section 32, thus creating gaps between the outer surface of the distal end 31A and the inner surface of the proximal portion 33A, allowing stomach acid from the pylorus-end chamber 104 to enter the lumen 28 through the gaps at the junction of the distal portion 31A and the proximal portion 33A.

A plurality of ribs 84 connect the proximal portion 33A of second section 32 to the distal portion 31A of the first section 30, preventing the second section 32 from slipping away from the distal portion 31A of the first section 30. The ribs 84 are integral to and connect the two portions 31A and 33A allowing the two walls of the two portions to be spaced apart for a limited distance. The trumpet-bell shaped opening 33 (the proximal end of the second section 32) includes an annular rim 86 sufficiently larger than the fully dilated opening of the pylorus 106, and of sufficient rigidity to prevent spontaneous passage of the annular rim 86 through the pylorus 106 caused by pulling forces in the distal direction created by peristaltic actions, thereby keeping the junction (the overlapping portion of the distal portion 31A and the proximal portion 33A) of the two sections 30 and 32 inside the pylorus 106 and providing an annular sealing around the inner circumference of the pylorus 106.

The rim 86 of the trumpet-bell shaped opening 33 also shares the pulling load exerted on the flange 20 of the funnel-shaped element 12, which is connected to the stomach wall. Other embodiments may use flaps cut into the wall of the tube 14 that swing inward with external pressure and seal to the tube wall with internal pressure to accomplish controlled entrance of stomach acid into the lumen 28 without exit of food. Still other embodiments may use one or more one-way check valves at the junction of the two sections 30 and 32.

The most preferred embodiment of the present invention will be designed for peroral implantation and explantation. The present invention further includes methods for treatment of obesity of a patient. In one preferred embodiment, the method will be performed as follows:

Preparation: An endoscopic suturing device such as the C. R. BARD ENDOCINCH™, or other endoscopic suturing device known to the art, will be used to place a plurality of sutures (10 to 12 sutures in a preferred embodiment) in the gastric cardiac region in a ring approximately 3 cm distal to the gastroesophageal junction. The sutures will be 2 m long polypropylene monofilament placed in a mattress configuration with a felt pledget. The suture tails, in pairs, will be passed through the circumference of the gastric bypass prosthesis (GBP) attachment ring flange using a free needle. A system of cut-away tubes (i.e. drinking straws) may be used to organize the strands and prevent suture pair entanglement.

Introduction: Suture pairs exiting the GBP flange will be taped together and identified by location. Each of the 10 to 12 pairs will be passed through the lumen of a 20 mm diameter hollow introducer tube. The GBP will be lubricated with hydrogel and stuffed in the distal end of the introducer tube (Cut-away organized tubes, if used, will be removed at this time.) The tube containing the GBP will be slid along the suture strand pairs in the same manner as an artificial heart valve is "parachuted" into place.

Deployment: Once the introducer tube clears the gastroesophageal sphincter, the GBP is ejected into the stomach by gently pushing from the distal end of the tube with a plastic rod. The suture pairs are cinched up to take up slack around half the diameter of the flange, but leaving a gap big enough for a 12 mm endoscope on one side. With the introducer tube withdrawn but the suture tails still in the esophagus, a 12 mm steerable endoscope is introduced through the esophagus and through the gap left at the edge of the GBP flange. The distal end of the GBP is visualized and captured using a grasper introduced through the endoscope instrument canal. The endoscope, with the distal end of the GBP attached, is maneuvered through the pyloric sphincter and the duodenum to the full length of the GBP where the distal end is released and the endoscope withdrawn.

Fixation: The endoscope is repositioned just proximal of the GBP attachment ring flange. The suture pairs are cinched up, closing off the gap formerly used by the endoscope. One by one, each pair of suture tails is tied with a sliding lock-knot (Dines knot, Roeder knot, etc.) facilitated by a knot-pusher to complete the 10 to 12 mattress stitches. The flange is then inspected via endoscope, and the suture tails are trimmed using micro-scissors through the endoscope instrument canal, and the endoscope removed. In other preferred embodiments, a circular anastomotic stapler such as the ETHICON PROXIMATE™ is used in place of suturing.

Explantation: This step entails endoscopic visualization of the GBP attachment flange, snipping the sutures at one side of the knot, and plucking the sutures out by the knot. The introducer tube, lubricated inside, is inserted past the gastroesophageal sphincter. A bent-wire hook is used to firmly engage one side of the attachment flange under endoscope visualization and pull it into the distal end of the introducer tube. When the wide flange portion of the GBP is fully enclosed by the introducer tube, the tube and GBP implant are pulled free of the GI tract as an assembly.

The invention may be embodied on other specific form without departing from the spirit or essential characteristics thereof. The present embodiments are therefore to be considered illustrative and not restrictive, the scope of the invention being dictated by the appended claims rather than by the foregoing description, and all changes which come within the meaning and range of equivalency of the claims are therefore intended to be embraced therein.

I claim:

1. A device for treatment of obesity of a patient comprising:
    an annular element having a relatively large outer boundary and a relatively small inner boundary;
    an elongated flexible tube extending between a proximal end and a distal end, said tube defining a central lumen within said tube, said proximal end of said tube being connected to said relatively small inner boundary of said annular element, and forming a continuous passageway through a region interior to said relatively small inner boundary and said lumen,
    wherein said relatively large outer boundary of said annular element is adapted to be attached to an inner wall of a stomach of said patient, such that said annular element divides said stomach into two chambers, an esophagus-end chamber close to an esophagus of said patient, and a pylorus-end chamber close to a pylorus of said patient, and wherein said esophagus-end chamber is in fluid communication with said lumen of said tube
    wherein at least a portion of said flexible tube is thin-walled and made of a flexible material such that the thin-walled portion collapses when subjected to a positive pressure differential from the outside of the tube to the inside of the tube, and is openable when subjected to a positive pressure differential from the inside of the tube to the outside of the tube, said flexible portion of said tube being adapted to transport food through said central lumen in response to musculature movement of said patient.

2. A device according to claim 1, wherein said annular element is flat.

3. A device according to claim 1, wherein said annular element is trumpet-shaped.

4. A device according to claim 1, wherein said annular element is a substantially conical-shaped element extending between a relatively large proximal end at said relatively large outer boundary and a relatively small distal end at said relatively small inner boundary, said conical-shaped element defining a hollow interior region extending between the two ends.

5. A device according to claim 1, wherein said esophagus-end chamber has an enclosed volume of about 30 to 70 ml.

6. A device according to claim 1, wherein said annular element defines an opening at said relatively small boundary, said opening connected to said lumen of said tube, wherein said opening has a diameter of about 0.8 to 1.5 cm.

7. A device according to claim 1, wherein said device further comprises a valve assembly disposed within said passageway near said proximal end of said tube for controlling opening and closing of said passageway.

8. A device according to claim 7, wherein said valve assembly opens when a pressure differential from a proximal side of said valve assembly to a distal side of said valve assembly is greater than a predetermined value, and said valve assembly closes when said pressure differential is less than the predetermined value.

9. A device according to claim 8, wherein said predetermined value is approximate to a pressure differential created by swallowing.

10. A device according to claim 8, wherein said predetermined value is about 5 mmHg to 30 mmHg.

11. A device according to claim 7, wherein said valve assembly comprises an one-way valve, allowing passage of food from a proximal side to a distal side of said valve and impeding passage of food from the distal side to the proximal side.

12. A device according to claim 7, wherein said valve assembly comprises a circular member attached to said relatively small boundary of said annular element, said circular member defining at least one slit cutting through said circular member, said slit being adapted for passage of food when expanded.

13. A device according to claim 7, wherein said valve assembly is characterized by hysteresis such that said valve assembly has an opening pressure differential across said valve assembly and a closing pressure differential across said valve assembly, said opening pressure differential being greater than said closing pressure differential.

14. A device according to claim 13, wherein said first predetermined value is a pressure differential created by swallowing.

15. A device according to claim 13, wherein said hysteresis means of said valve assembly comprises: an elastic hinge element extending from an inner surface of said tube; a plug element attached to said hinge element, wherein said plug element is sized to close said passageway; a protrusion extending from a distal side of said plug element to a distal end; and a bump extending from said inner surface of said tube, said bump defining a socket in said bump, wherein said distal end of said protrusion rests in said socket when said plug element closes said passageway, wherein when the pressure differential reaches the first predetermined value, the pressure differential causes said plug element to swing toward the distal end of the tube and thereby causes said protrusion to snap over said bump, when said pressure differential reaches said second predetermined value, said elastic hinge element causes said plug element to swing up to close said passageway.

16. A device according to claim 7, wherein said valve assembly comprises means for sensing opening and closing of the pylorus, and wherein said valve assembly is adapted to open and close said passageway corresponding to the opening and closing of the pylorus.

17. A device according to claim 7, wherein said valve assembly comprises means for detecting digestive juices in a digestive tract of the patient, and wherein said valve assembly is adapted to open and close said passageway in response to the detected digestive juices.

18. A device according to claim 7, wherein said valve assembly comprises means for detecting hormones in a digestive tract of the patient, and wherein said valve assembly is adapted to open and close said passageway in response to the detected hormones.

19. A device according to claim 1, wherein said annular element is flexible.

20. A device according to claim 1, wherein at least a portion of said flexible tube is thin-walled and made of a flexible material such that the thin-walled portion collapses to a substantially flat condition when subjected to a positive pressure differential from the outside of the tube to the inside of the tube.

21. A device according to claim 1, wherein said flexible tube includes two sections, a first section connected to the relatively small inner boundary of said annular element, and a second section connected to a distal end of said first section, wherein said first section has a length such that when said device is attached to the inner wall of the stomach, said first section extends to the pylorus of said patient, wherein said second section is thin-walled and made of a flexible material such that the second section collapses to a substantially flat condition when the pressure outside the second section is greater than the pressure inside the second section.

22. A device according to claim 21, wherein said first section is made of a flexible material such that when the pressure differential from the outside of the first section to the inside the first section is greater than a predetermined value, said first section collapses to a substantially flat condition.

23. A device according to claim 21, wherein said first section is accordion-like shaped such that the length of said first section compresses and expands without substantial change to the diameter of said lumen within said first section.

24. A device according to claim 21, wherein said device comprising a first valve assembly disposed near the proximal end of said tube, and a second valve assembly disposed at the distal end of said first section, wherein said valve assemblies are adapted for opening and closing said passageway.

25. A device according to claim 1, wherein said flexible tube has a length of about 50 to 200 cm.

26. A device according to claim 1, wherein said flexible tube has a length such that when said device is attached to the stomach of the patient, said tube extends beyond the pylorus of said patient.

27. A device according to claim 1, wherein said relatively large outer boundary of said annular element is adapted to be attached to the inner wall of the stomach by sutures.

28. A device according to claim 1, wherein said relatively large outer boundary is adapted to be attached to the inner wall of the stomach by staples.

29. A device according to claim 1, wherein said relatively large outer boundary is adapted to be attached to the inner wall of the stomach by adhesive.

30. A device according to claim 1, wherein said relatively large outer boundary is adapted to be attached to the inner wall of the stomach by any combination of sutures, staples, and adhesive.

31. A device according to claim 1, wherein said annular element includes an annular flange extending from said relatively large outer boundary of said annular element, said annular flange is adapted to be attached to the inner wall of the stomach.

32. A device according to claim 31, wherein said flange is reinforced with a fibrous material.

33. A device according to claim 1, wherein said flexible tube is accordion-like shaped such that the length of said tube compresses and expands without substantial change to the diameter of said lumen within said flexible tube.

34. A device according to claim 1, wherein said annular element is adapted to be attached to the inner wall of an upper portion the stomach, which is close to the esophagus of the patient.

35. A device according to claim 1, wherein said relatively large outer boundary of said annular element has a diameter which is smaller than the diameter of a portion of the stomach where the annular element is to be attached, such that when said annular element is attached to the inner wall of said portion, said portion of said stomach is constricted.

36. A device according to claim 1, wherein said tube comprises a flexible portion which passes through the pylorus of the patient such that when the pylorus constricts, said portion is compressed so that said passageway is closed by the pylorus.

37. A device according to claim 1, wherein said tube comprises a portion that passes through the pylorus of the patient, said portion comprising channels for conducting fluid from stomach to intestine.

38. A device according to claim 1, wherein said tube defines at least one one-way channel on a lateral wall of said tube, said one-way channel allowing passage of fluid from a digestive tract of said patient into said lumen and impeding passage of food from said lumen to said digestive tract.

39. A device according to claim 1, wherein said tube comprises two sections, a first section extending from said distal end of said annular element, and a second section, wherein said first section includes a flexible distal portion which diameter tapers to its distal end, and wherein said second section includes a trumpet-bell shaped proximal portion at a proximal end of said second section, and wherein said distal portion of said first section is inserted into said proximal portion of said second section and is connected to the second section by connecting means, forming an overlapping portion, said overlapping portion passing through the pylorus of the patient when the device is attached to the stomach, such that when the pressure inside said overlapping portion is greater than the pressure outside the overlapping portion, walls of said flexible distal portion expands and in tight contact with walls of said proximal portion, and when the pylorus compresses said overlapping portion, said flexible distal portion of said first section collapses, creating at least one gap between said distal portion and said proximal portion for conducting fluid from the pylorus-end chamber into the second section.

40. A device for treatment of obesity of a patient comprising;
an annular element having a relatively large outer boundary and a relatively small inner boundary; an elongated flexible tube extending between a proximal end and a distal end, said tube defining a central lumen within said tube, said proximal end of said tube being connected to said relatively small boundary of said annular element, and forming a continuous passageway through a region interior to said relatively small boundary and said lumen,
wherein said relatively large outer boundary of said annular element includes fibrous is adapted to be attached to an inner wall of a stomach of said patient, such that said annular element divides said stomach into two chambers, an esophagus-end chamber close to an esophagus of said patient, and a pylorus-end chamber close to a pylorus of said patient, and wherein said esophagus-end chamber is in fluid communication with said lumen of said tube, wherein said flexible tube includes two connected sections,
wherein said first section has a length such that when said device is attached to the inner wall of the stomach, said first section extends from the relatively small inner boundary of said annular element to the pylorus of said patient, wherein said second section is made of a flexible material and is thin-walled such that said second section collapses to a substantially flat condition when the pressure outside the second section is greater than the pressure inside the second section and is openable when subjected to a positive pressure differential from the inside of the tube to the outside of the tube, said flexible portion of said tube being adapted to transport food through said central lumen in response to musculature movement of said patient.

41. A device according to claim 40, wherein said device fisher comprises a valve 25 assembly disposed within said passageway near said proximal end of said tube, wherein said valve assembly is adapted for opening and closing said passageway.

42. A device according to claim 40, wherein said valve assembly opens when a pressure differential from a proximal side of said valve assembly to a distal side of said valve assembly reaches a pressure differential created by swallowing, and remains closed when the pressure differential across the valve assembly is less than the pressure differential created by swallowing.

43. A device according to claim 21, wherein said first section is accordion-like shaped such that the length of said first section compresses and expands without substantial change to the diameter of said lumen within said first section.

44. A method for treatment of obesity of a patient comprising:
providing an annular element having a relatively large outer boundary and a relatively small inner boundary, and an elongated flexible tube extending between a proximal end and a distal end, said tube being connected at said proximal end to said relatively small inner boundary of said annular element, said tube defining a central lumen within said tube,
inserting an annular element and said tube into a stomach of the patient; and
attaching said relatively large outer boundary of said annular element to an inner circumference of the stomach of said patient, such that said annular element divides said stomach into two chambers, an esophagus-end chamber close to an esophagus of said patient, and a pylorus-end chamber close to a pylorus of said patient, and whereby said esophagus-end chamber is in fluid communication with said lumen of said tube;
wherein at least a portion of said flexible tube is thin-walled and made of a flexible material such that the thin-walled portion collapses when subjected to a positive pressure differential from the outside of the tube to the inside of the tube, and is openable when subjected to a positive pressure differential from the inside of the tube to the outside of the tube, said flexible portion of said tube being adapted to transport food through said central lumen in response to musculature movement of said patient.

45. A method according to claim 44, wherein said inner circumference is at an upper portion of said stomach which is close to the esophagus of said patient.

46. A method according to claim 44, wherein said annular element further comprising an elongated flexible tube extending from the relatively small inner boundary in a distal direction, and wherein said method further comprising placing said elongated tube in an intestine of said patient.

* * * * *

UNITED STATES PATENT AND TRADEMARK OFFICE
CERTIFICATE OF CORRECTION

PATENT NO. : 7,316,716 B2  Page 1 of 1
APPLICATION NO. : 10/511385
DATED : January 8, 2008
INVENTOR(S) : Thomas D. Egan It is certified that error appears in the above-identified patent and that said Letters Patent is hereby corrected as shown below:

1. Title page of the patent, please include the following domestic priority data:
-- 60/379,160 May 9, 2002 --

2. At Column 18, Line 2, should read as follows:
-- annular element is adapted to be --

3. At Column 18, Line 37, should read as follows:
-- A device according to claim 40, wherein said first --

Signed and Sealed this

First Day of July, 2008

JON W. DUDAS
*Director of the United States Patent and Trademark Office*